United States Patent [19]

Ōe et al.

[11] Patent Number: 4,465,681
[45] Date of Patent: Aug. 14, 1984

[54] BIS-(AMINOALKOXY)-PHENYL, PYRIDYL KETONES, AND USE AS IMMUNOLOGICAL AGENTS

[75] Inventors: Takanori Ōe, Nakatsu; Mineo Tsuruda, Shiidamachi; Kazuhiro Goto; Masao Hisadome, both of Nakatsu, all of Japan

[73] Assignee: Yoshitomi Pharmaceutical Industries Ltd., Japan

[21] Appl. No.: 403,664

[22] PCT Filed: Dec. 9, 1981

[86] PCT No.: PCT/JP81/00374
§ 371 Date: Jul. 28, 1982
§ 102(e) Date: Jul. 28, 1982

[87] PCT Pub. No.: WO82/02045
PCT Pub. Date: Jun. 24, 1982

[30] Foreign Application Priority Data

Dec. 10, 1980 [JP] Japan .................. 55-175108

[51] Int. Cl.$^3$ .................. A61K 31/44; C07D 213/64
[52] U.S. Cl. .................. 424/248.4; 424/248.58; 424/250; 424/263; 424/267; 544/121; 544/124; 544/257; 544/360; 546/187; 546/194; 546/283; 546/290; 546/298; 546/300; 546/301
[58] Field of Search .............. 546/290, 298, 187, 194, 546/283, 300, 301; 544/121, 124, 257, 360; 424/248.4, 248.58, 250, 263, 267

[56] References Cited
FOREIGN PATENT DOCUMENTS
56-100765 8/1981 Japan .

OTHER PUBLICATIONS
Chemical Abstracts, vol. 96, 3509v, (1982).
Central Patent Index, Abstract No. 70795 D/39.

Primary Examiner—Henry R. Jiles
Assistant Examiner—J. G. Mullins
Attorney, Agent, or Firm—Larson and Taylor

[57] ABSTRACT

Pyridine derivatives of the formula:

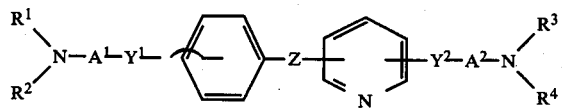

or pharmaceutically acceptable acid addition salts thereof, wherein $R^1$, $R^2$, $R^3$ and $R^4$ are the same or different and each represents hydrogen atom or lower alkyl group, or $R^1$ and $R^2$, or $R^3$ and $R^4$ together with the adjacent nitrogen atom form a heterocycle, $A^1$ and $A^2$ are the same or different and each represents alkylene or hydroxy-substituted alkylene group, $Y^1$ and $Y^2$ are the same or different and each represents oxygen or sulfur atom, and Z represents

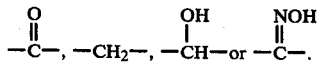

These compounds show pharmacological activities such as potentiating activity for leukocyte phagocytosis, potentiating activity for macrophage phagocytosis, potentiating activity for the production of rosette forming cells in the spleen and anti-adjuvant arthritis activity, and are useful as medicines.

12 Claims, No Drawings

BIS-(AMINOALKOXY)-PHENYL, PYRIDYL KETONES, AND USE AS IMMUNOLOGICAL AGENTS

TECHNICAL FIELD AND DISCLOSURE OF THE INVENTION

This invention relates to novel pyridine derivatives which are useful as medicines and are represented by the formula:

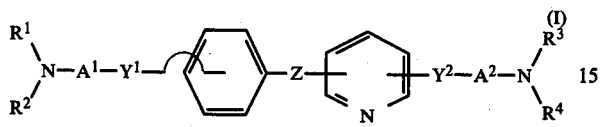

and salts thereof.

In the above formula, $R^1$, $R^2$, $R^3$ and $R^4$ are the same or different and each represents hydrogen atom or lower alkyl group such as methyl, ethyl, propyl, isopropyl, butyl, isobutyl, sec-butyl or tert-butyl, or $R^1$ and $R^2$, or $R^3$ and $R^4$ together with the adjacent nitrogen atom form a heterocycle such as pyrrolidine, piperidine, piperazine, 4-methylpiperazine, 4-(hydroxyethyl)-piperazine, morpholine or imidazole, $A^1$ and $A^2$ are the same or different and each represents straight or branched alkylene group such as methylene, ethylene, propylene, trimethylene or tetramethylene or hydroxy-substituted alkylene group such as 2-hydroxytrimethylene, $Y^1$ and $Y^2$ are the same or different and each represents oxygen or sulfur atom, and Z is —CO—, —CH$_2$—, —CH(OH)— or —C(=NOH)—.

The pyridine derivatives of the present invention can be produced by the following methods, for example.

METHOD 1

This method, to be applied for the production of compounds of formula (I) wherein Z is —CO—, comprises reacting a compound of the formula:

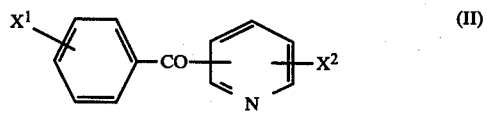

wherein $X^1$ and $X^2$ are the same or different and each represents halogen atom such as fluorine, chlorine or iodine, with a compound of the formula:

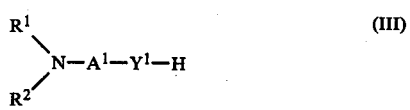

wherein each symbol is as defined above.

The reaction proceeds in a solvent such as dimethylformamide, dimethyl sulfoxide, hexamethylphosphoramide, toluene, xylene, lower alkanol or pyridine at $-10°$ C. to $150°$ C. Moreover, the reaction is preferably carried out by using a starting material (III) of which the active hydrogen atom is converted into the alkali metal salt by the use of sodium hydride, sodium amide, sodium alkoxide, sodium hydroxide, potassium hydroxide or the like, or in the presence of an acid acceptor such as potassium carbonate or sodium carbonate.

When the reaction is carried out by one step, compounds of formula (I) wherein $(R^1)(R^2)N-A^1-Y^1-$ and $(R^3)(R^4)N-A^2-Y^2-$ are identical are obtained. However, it is possible to obtain compounds wherein both the groups are different each other by carrying out the reaction stepwise under the reaction conditions suitably selected. For instance, the reaction of 2-chloro-3(4-fluorobenzoyl)pyridine of the formula:

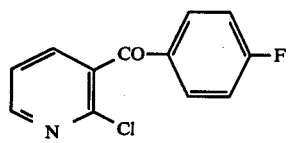

with an equimolecular amount of a compound of formula (III) in toluene gives a compound of the formula:

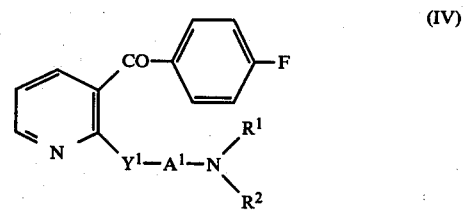

and the said reaction in dimethylformamide gives a compound of the formula:

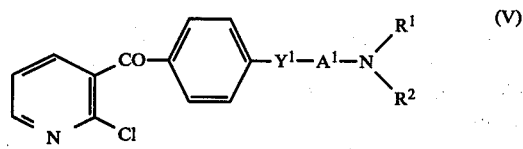

Compound (IV) or (V) is reacted with a compound which is different to compound (III) and has the formula:

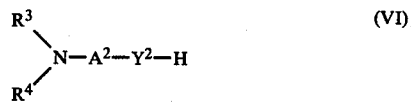

wherein each symbol is as defined above, under the conditions mentioned above to give compound (I). It goes without saying that a compound (IV) or (V) can be reacted, after or without isolation, with the same starting material (III).

When a compound (III) or (VI) wherein A represents a hydroxy-substituted alkylene is used as a starting material in all of the above reactions, it is desirable that the compound of which the hydroxy group is protected by an acyl group such as acetyl, propionyl, pivaloyl or benzoyl or by forming an oxazolidine ring (e.g. as a compound (III), the compound of the formula:

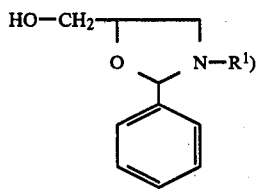

is used in the reaction, and then the final reaction product is hydrolyzed to eliminate the protecting group by an acid or alkali such as hydrochloric acid, sulfuric acid, potassium carbonate or sodium hydroxide.

METHOD 2

This method, to be applied for the production of compounds of formula (I) wherein Z is —$CH_2$— or —CH(OH)—, comprises reducing a compound of formula (I) wherein Z is —CO—.

The reduction is carried out by a conventional method such as reduction with a complex metal hydride (e.g. sodium borohydride or lithium aluminium hydride), reduction with sodium amalgam, Clemmensen reduction, Wolff-Kishner reduction or catalytic reduction, in a solvent such as methanol, ethanol, isopropanol, water, ether, tetrahydrofuran or a mixture thereof.

METHOD 3

This method, to be applied for the production of compounds of formula (I) wherein Z is —C(=NOH)—, comprises reacting a compound of formula (I) wherein Z is —CO— with hydroxylamine in a solvent such as methanol, ethanol, isopropanol, water or a mixture thereof.

The compounds of formula (I) thus obtained can form salts in a conventional manner with organic acids such as maleic acid, tartaric acid, fumaric acid, oxalic acid, succinic acid, methanesulfonic acid and toluene-sulfonic acid or inorganic acids such as hydrochloric acid, hydrobromic acid, sulfuric acid and phosphoric acid.

The compounds of formula (I) show pharmacological activities such as potentiating activity for leukocyte phagocytosis, potentiating activity for macrophage phagocytosis, potentiating activity for the production of rosette forming cells in the spleen and anti-adjuvant arthritis activity.

Pharmacological activities of the compounds of the present invention are shown below:

TEST COMPOUNDS

A: 2,4′-bis(2-dimethylaminoethoxy)-3-benzoylpyridine dihydrochloride hemihydrate
B: 2,4′-bis(1-methyl-2-dimethylaminoethoxy)-3-benzoylpyridine dioxalate

EXPERIMENT 1

Anti-adjuvant arthritis activity in rats (A model disease of rheumatoid arthritis)

Male Lewis rats (8–9 weeks old) were used. Adjuvant arthritis was caused by the method described by B. B. Newbould in "Brit. J. Pharmacol.", 21, 127 (1963). Twenty-one days after the subcutaneous injection of a suspension of killed tubercle bacillus in Freund's adjuvant into the tail of the rats, the severity of arthritis was assayed as the hindleg volume. Each group of the rat was orally administered with the test compound once a day. The results are shown in Table 1.

TABLE 1

| Test Compound | Dose (mg/kg) | Volume of Hindleg (ml) |
|---|---|---|
| Control | 0 | 2.40 ± 0.20 |
| A | 50 | 1.17 ± 0.29** |

**$p < 0.01$ significant vs control

It was confirmed that the treatment with Test compound A resulted in a significant inhibition of adjuvant arthritis at a dose of 50 mg/kg. Therefore, Test compound A has anti-arthritis activity.

EXPERIMENT 2

Activity for suppressing immune response in BALB/C strain mice

Female BALB/C strain mice (6 weeks old) were used by dividing into groups of 6 animals. The sensitization was made by intraperitoneal injection of antigen: $5 \times 10^8$ sheep red blood cells. Each mouse was orally administered with the test compound on the same day and the next day of the sensitization. Four days after the sensitization, the number of plaque-forming cells (PFC) in the spleen, and the number of rosette-forming cells (RFC) in the spleen and/or thymus were measured in a usual manner. The results are shown in Table 2.

TABLE 2

| Treatment | Dose (mg/kg) | No. of PFC ($\times 10^4$) Spleen | No. of RFC ($\times 10^4$) Spleen | No. of RFC ($\times 10^4$) Thymus |
|---|---|---|---|---|
| Control | 0 | 17.4 ± 2.3 | 135 ± 27 | 9.5 ± 1.0 |
| A | 30 | 9.0 ± 1.4** | 126 ± 24 | 1.2 ± 0.4** |
| Control | 0 | 9.5 ± 1.0 | 172 ± 32 | — |
| B | 30 | 4.6 ± 0.8** | 88 ± 10** | — |

**$p < 0.01$ significant vs control

The treatment with the test compound resulted in the reduction of PFC in the spleen, and RFC in the spleen or thymus. The results show that the test compound has an immunosuppressive activity in BALB/C strain mice.

EXPERIMENT 3

Activity for potentiating immune response in C57BL/6 strain mice

Female C57BL/6 strain mice (6 weeks old) were used dividing into groups of 6 animals. The sensitization was made by intraperitoneal injection of antigen: $5 \times 10^8$ sheep red blood cells. Each mouse was orally administered with the test compound on the same day and next day of the sensitization. Six days after the sensitization, the number of rosette-forming cells (RFC) in the spleen and/or thymus was measured in a usual manner. The results are shown in Table 3.

TABLE 3

| Treatment | Dose (mg/kg) | No. of RFC ($\times 10^4$) Spleen | No. of RFC ($\times 10^4$) Thymus |
|---|---|---|---|
| Control | 0 | 75 ± 17 | 2.8 ± 0.5 |
| A | 30 | 214 ± 46** | 7.4 ± 1.1** |
| Control | 0 | 55 ± 11 | — |
| B | 30 | 149 ± 22** | — |

**$p < 0.01$ significant vs control

The treatment with the test compound resulted in the increase of RFC in the spleen or thymus. The results show that the test compound has an immunopotentiating activity in C57BL/6 strain mice.

EXPERIMENT 4

Activation of peritoneal macrophage in mice

Peritoneal macrophages were obtained from male dd mice (8 weeks old). After washing macrophages, the cells were adjusted to $5 \times 10^6$ macrophages/ml in Hanks' solution. A mixture containing 100 μl of the macrophage suspension, 50 μl of mice serum and 10 μl of the test compound was preincubated at 37° C. for 10 minutes, and then 50 μl of yeast cells ($2.5 \times 10^8$/ml) was added thereto. After further incubation of the mixture at 37° C. for 20 minutes, the number of macrophages phagocytosing yeast was counted in a usual manner. The results are shown in Table 4.

TABLE 4

| Test Compound | Phagocytosis (%) | | | |
|---|---|---|---|---|
| | 0 | 10 | 30 | 100 μM |
| A | 33.9 ± 0.8 | 35.5 ± 1.9 | 46.5 ± 2.7** | 54.3 ± 3.1** |
| B | 33.9 ± 0.8 | 40.8 ± 2.7 | 49.6 ± 2.1** | 63.4 ± 6.7** |

**$p < 0.01$ significant vs control

The results show that the test compound has a macrophage-activating capacity. Therefore, the test compounds may potentiate host defense activity against infections.

EXPERIMENT 5

Acute toxicity

Acute toxicity was determined using male dd mice (8 weeks old). The results are shown in Table 5.

TABLE 5

| Test Compound | Route | $LD_{50}$ (mg/kg) |
|---|---|---|
| A | p.o. | >1000 (1/6)[a] |
| | i.p. | 300 |
| B | p.o. | >1000 (0/5)[a] |
| | i.p. | 250 |

[a]dead/total animals

The compounds of the present invention when used as medicines can be administered orally or parenterally in the form of powders, granules, tablets, capsules, injectable solutions or the like admixed with pharmaceutically acceptable and suitable carrier, vehicle, diluent or the like. The dose, which may vary depending upon the kind of diseases and symptom, is usually about 10–1000 mg per day for adults.

An example of pharmaceutical preparations is shown below.

100 mg Tablets are prepared from the following compositions:

| Compound of the Invention | 100 mg |
|---|---|
| Lactose | 74 mg |
| Starch | 30 mg |
| Microcrystalline Cellulose | 20 mg |
| Talc | 5 mg |
| Magnesium Stearate | 1 mg |
| Total | 230 mg |

The present invention will be further illustrated in detail by the following examples, but they are not to be construed as limiting the present invention.

EXAMPLE 1

50% Sodium hydride (2.3 g) is suspended in 30 ml of dimethylformamide whereupon 7 g of dimethylaminoethanol is added, and the resulting mixture is stirred at room temperature until the evolution of hydrogen gas ceases. 2-Chloro-3-(4-fluorobenzoyl)pyridine (5 g) is then added, and the whole is stirred at 35°–40° C. for 2 hours. Water is added to the reaction mixture and extracted with toluene. The toluene layer is washed with water and dried, and the toluene is distilled off. A solution of oxalic acid in alcohol is added to the residual oil. The product crystallized out is purified with aqueous methanol to give 2,4'-bis(2-dimethylaminoethoxy)-3-benzoylpyridine dioxalate, melting at 193°–194° C. with decomposition. The corresponding dihydrochloride hemihydrate shows a melting point of 166°–168° C. (ethanol-ethyl acetate).

EXAMPLE 2

To free hydroxylamine prepared by adding 4.3 g of hydroxylamine hydrochloride to a solution of 2.5 g of sodium hydroxide in 7 ml of water are added 50 ml of ethanol and 4.5 g of 2,4'-bis(2-dimethylaminoethoxy)-3-benzoylpyridine, and the resulting mixture is heated at 70°–80° C. for 4 hours. After the reaction is completed, the ethanol is distilled off under reduced pressure. Water is added to the residue and extracted with toluene. The toluene layer is washed with water and dried, and the toluene is distilled off. The residue is purified on a column of silica gel, and recrystallized from ether to give 2,4'-bis(2-dimethylaminoethoxy)-3-benzoylpyridine ketoxime, melting at 84°–86° C.

EXAMPLE 3

(a) Dimethylformamide (30 ml), 7.1 g of 50% sodium hydride, 17 g of ethylaminoethanol and 15 g of 2-chloro-3-(4-fluorobenzoyl)pyridine are reacted and post-treated in a similar manner of Example 1, and the reaction product is converted into the maleate in ethyl acetate. The product is purified with ethyl acetate - ethanol mixtures to give 2,4'-bis(2-ethylaminoethoxy)-3-benzoylpyridine dimaleate, melting at 138°–139° C.

(b) 50% Sodium hydride (1.7 g) is added to 50 ml of toluene followed by addition of 5.3 g of ethylaminoethanol. After stirring at room temperature for 2 hours, the evolution of hydrogen gas almost ceases. 2-Chloro-3-(4-fluorobenzoyl)pyridine (7.1 g) is then added with ice-water cooling, and the resulting mixture is stirred at 10° C. for 30 minutes and then at 25°–30° C. for 3 hours. Water is then added to the reaction mixture. The toluene layer is separated and extracted with dilute hydrochloric acid. The acid extract is made alkaline with potassium carbonate and extracted again with toluene. The toluene separated is distilled off, and the residue is purified on a column of silica gel to give oily 2-(2-ethylaminoethoxy)-3-(4-fluorobenzoyl)pyridine (M.p. of the oxalate: 162°–164° C.).

2-(2-Ethylaminoethoxy)-3-(4-fluorobenzoyl)pyridine (2.8 g), 15 ml of dimethylformamide, 0.6 g of 50% sodium hydride and 1.8 g of ethylaminoethanol are reacted and post-treated in a similar manner of Example 1 to give 2,4'-bis(2-ethylaminoethoxy)-3-benzoylpyridine (M.p. of the dimaleate: 138°–139° C.).

EXAMPLE 4

2,4'-Bis(2-ethylaminoethoxy)-3-benzoylpyridine (4.5 g) is dissolved in 30 ml of ethanol whereupon 0.5 g of sodium borohydride is added, and the resulting mixture is stirred at 35°–40° C. for 4 hours. After the reaction is completed, the ethanol is distilled off. Water is added to the residue and extracted with toluene. The toluene layer is washed with water and dried, and the toluene is distilled off. The residue is converted into the oxalate in methanol. The product is purified with aqueous methanol to give α-[2-(2-ethylaminoethoxy)pyridin-3-yl]-p-(2-ethylaminoethoxy)benzyl alcohol dioxalate, melting at 173° C. with decomposition.

EXAMPLE 5

50% Sodium hydride (5.6 g) is suspended in 40 ml of dimethylformamide whereupon 34.5 g of 2-phenyl-3-tert-butyl-5-hydroxymethyloxazolidine is added, and the resulting mixture is stirred at room temperature for 1 hour. 2-Chloro-3-(4-fluorobenzoyl)pyridine (11.5 g) is then added, and the whole is stirred at 35°-40° C. for 2 hours. Water is then added to the reaction mixture. The oil separated is extracted with 100 ml of toluene. After the toluene is washed with water, 200 ml of 1N-hydrochloric acid is added, and the resulting mixture is warmed at 60°-65° C. with vigorous stirring for 30 minutes to hydrolyze the reaction product. The aqueous layer is separated, made alkaline with potassium carbonate and extracted with chloroform. The chloroform layer is washed with water and dried, and the chloroform is distilled off. The residual oil is dissolved in metahnol and converted into the oxalate by adding a solution of oxalic acid in methanol. The product is purified with aqueous isopropanol to give 2,4'-bis(3-tert-butylamino-2-hydroxypropoxy)-3-benzoylpyridine dioxalate, melting at 199°-200° C. with decomposition.

EXAMPLE 6

(a) Dimethylformamide (25 ml), 2.3 g of 50% sodium hydride, 7 g of 3-dimethylaminopropanol and 5 g of 2-chloro-3-(4-fluorobenzoyl)pyridine are reacted and post-treated in a similar manner of Example 1, and the reaction product is converted into the oxalate in methanol. The product is purified with methanol to give 2,4'-bis(3-dimethylaminopropoxy)-3-benzoylpyridine dioxalate, melting at 164°-165° C.

(b) 50% Sodium hydride is suspended in 30 ml of dimethylformamide whereupon 5 g of 3-dimethylaminopropanol is added, and the resulting mixture is stirred at room temperature for 1 hour. 2-Chloro-3-(4-fluorobenzoyl)-pyridine (5 g) is then added under cooling, and the whole is stirred at 10° C. for 30 minutes and then at 25°-35° C. for 2 hours. Water is then added to the reaction mixture and extracted with toluene. The toluene layer is extracted with dilute hydrochloric acid, and the acidic extract is made alkaline with potassium carbonate. The aqueous layer is extracted again with toluene. The toluene is distilled off, and the residue is purified on a column of silica gel to give oily 2-chloro-3-[4-(3-dimethylaminopropoxy)-benzoyl]pyridine (M.p. of the oxalate: 188°-190° C. (decomposition).

2-Chloro-3-[4-(3-dimethylaminopropoxy)benzoyl]-pyridine (1.5 g), 10 ml of dimethylformamide, 0.3 g of 50% sodium hydride and 1 g of 3-dimethylaminopropanol are reacted and post-treated in a similar manner of Example 1 to give 2,4'-bis(3-dimethylaminopropoxy)-3-benzoylpyridine (M.p. of the dioxalate: 164°-165° C).

The following compounds are produced by the similar methods of the above examples:

(7) 2,4'-Bis(2-dimethylaminoethoxy)-3-benzoylpyridine dioxalate, m.p. 182°-184° C. (decomposition)
(8) 2,4'-Bis(2-morpholinoethoxy)-3-benzoylpyridine, m.p. 87° C.
(9) 2,4'-Bis(2-dimethylaminoethoxy)-5-benzoylpyridine dihydrochloride, m.p. 234°-235° C. (decomposition)
(10) 2,4'-Bis[2-(1-imidazolyl)ethoxy]-3-benzoylpyridine, m.p. 90°-92° C.
(11) 2,4'-Bis[3-(1-imidazolyl)propoxy]-3-benzoylpyridine, m.p. 109°-111° C.
(12) 2,4'-Bis[2-(1-imidazoyl)ethoxy]-5-benzoylpyridine, m.p. 65°-68° C.
(13) 2,4'-Bis(2-dimethylaminoethylthio)-3-benzoylpyridine dioxalate, m.p. 204°-205° C. (decomposition)
(14) 2,4'-Bis(1-methyl-2-dimethylaminoethoxy)-3-benzoylpyridine dioxalate, m.p. 143°-145° C.
(15) 2,4'-Bis(2-dimethylaminoethoxy)-3-benzylpyridine
(16) 2-(2-Dimethylaminothoxy)-4'-(3-dimethylaminopropoxy)-3-benzoylpyridine Although the present invention has been adequately discussed in the foregoing specification and examples included therein, one readily recognizes that various changes and modifications may be made without departing from the spirit and scope thereof.

What is claimed is:

1. Pyridine derivatives of the formula:

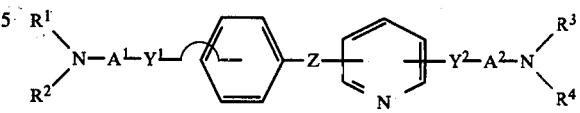

or pharmaceutically acceptable acid addition salts thereof, wherein $R^1$, $R^2$, $R^3$ and $R^4$ are the same different and each represents hydrogen atom or lower alkyl group, or $R^1$ and $R^2$, or $R^3$ and $R^4$ together with the adjacent nitrogen atom form a heterocyclic radical selected from the group consisting of pyrrolidino, pipeeridino, 4-methyl-piperazino, 4-hydroxyethyl-piperazino, morpholino, or imidazolyl,- , and $A^1$ and $A^2$ are the same or different and each represents alkylene or hydroxy-substituted alkylene group, $Y^1$ and $Y^2$ are the same or different and each represents oxygen or sulfur atom, and Z represents

2. The compound of claim 1: 2,4'-Bis(2-dimethylaminoethoxy)-3-benzoylpyridine.

3. The compound of claim 1: 2,4'-Bis(2-ethylaminoethoxy)-3-benzoylpyridine.

4. The compound of claim 1: 2,4'-Bis(3-dimethylaminopropoxy)-3-benzoylpyridine.

5. The compound of claim 1: 2,4'-Bis(2-diethylaminoethoxy)-3-benzoylpyridine.

6. The compound of claim 1: 2,4'-Bis[2-(1-imidazolyl)ethoxy]-3-benzoylpyridine.

7. The compound of claim 1: 2,4'-Bis(2-dimethylaminoethylthio)-3-benzoylpyridine.

8. The compound of claim 1: 2,4'-Bis(1-methyl-2-dimethylaminoethoxy)-3-benzoylpyridine.

9. A pharmaceutical composition containing a compound of claim 1 in an amount effective to stimulate phagocytic activity in leukocytes and a pharmaceutically acceptable carrier.

10. A pharmaceutical composition containing a compound of claim 1 in an amount effective to stimulate phagocytic activity in macrophages and a pharmaceutically acceptable carrier.

11. A pharmaceutical composition containing a compound of claim 1 in an amount effective to stimulate the production of rosette-forming cells in the spleen and a pharmaceutically acceptable carrier.

12. A pharmaceutical composition containing a compound of claim 1 in an amount effective to stimulate anti-adjuvant arthritis activity in the immunological system of mammals and a pharmaceutically acceptable carrier.

* * * * *